United States Patent [19]

Le Noir

[11] 4,067,340

[45] Jan. 10, 1978

[54] SURGICAL INSTRUMENT FOR MENISCECTOMY AND METHOD OF USING THE SAME

[76] Inventor: James L. Le Noir, 4500 Magnolia St., Suite 335, New Orleans, La. 70115

[21] Appl. No.: 668,361

[22] Filed: Mar. 19, 1976

[51] Int. Cl.² .............................................. A61B 17/32
[52] U.S. Cl. ..................................................... 128/305
[58] Field of Search .................. 128/305, 309; 30/272, 30/286

[56] References Cited

U.S. PATENT DOCUMENTS

| 1,339,692 | 5/1920 | Diamant | 128/309 |
| 2,258,287 | 10/1941 | Grieshaber | 128/309 |
| 2,843,128 | 7/1958 | Storz | 128/309 |

FOREIGN PATENT DOCUMENTS

| 853,410 | 12/1938 | France | 128/309 |

Primary Examiner—Stephen C. Pellegrino
Assistant Examiner—Michael H. Thaler
Attorney, Agent, or Firm—William D. Hall; Geoffrey R. Myers

[57] ABSTRACT

A surgical instrument for performing a meniscectomy comprising a pair of curved grooved guides of a shape corresponding to the periphery of the relatively inaccessible posterior portion of the meniscus, each guide being on a separate handle so that the two guides can be inserted intra-articularly respectively above and below the posterior portion of the meniscus to be peripherally detached. The two separate handles may then first be rigidly attached to each other and secondly to an overlying cutting blade frame. The cutting blade frame extends along the length of the grooved blade guide handles to the base of the two grooved guides and continuous upward after being bent through an angle of approximately 100° with the cutting blade base mount. The continuation of this cutting blade frame supports and contains the flexible cutting blade which may be driven by any suitable force-producing means, for example, a mechanism operated on the screw-jack principle. When so driven the flexible cutting blade advances or proceeds along the grooves in the aforesaid curved grooved guides and detaches the periphery of the meniscus near its base intra-articularly along a curved path corresponding to the shape of said curved grooved guides. A surgical procedure for detaching a meniscus, using the above-mentioned instrument is described in detail.

37 Claims, 15 Drawing Figures

SURGICAL INSTRUMENT FOR MENISCECTOMY AND METHOD OF USING THE SAME

BACKGROUND OF THE INVENTION

The critical need for a better surgical instrument and a better technique for detaching the posterior portion of the menisci (both medial and lateral) has long been recognized. No difficulty is encountered in removal of the anterior portion (i.e. in front of the collateral ligament) since it is readily visible and is easily accessible for sharp dissection detachment. The posterior portion of the menisci (i.e. behind the collateral ligament) is an entirely different matter. It is not visible and is almost inaccessible; hence, a precise controlled detachment at the periphery of the meniscal base is impossible with prior art methods and instruments. Present instruments (i.e. Lowe-Breck and Smillie knives) are essentially a handle with a curved shaft having a concave sharpened end which is pushed manually more or less blindly around the periphery of the meniscus in an attempt to detach the meniscus. Most often the synovial attachment to the meniscus is mutilated as is the meniscus. These instruments are mechanically ineffective and damaging to the posterior knee joint. Even when a second incision is made behind the collateral ligament in an attempt to obtain clearer view of the posterior part of the meniscus, the small incision, compactness of the anatomic structures and the depth of the meniscus again make the use of the Lowe-Breck and Smillie knives imprecise, mechanically difficult, and damaging. The mechanical performance of these knives leave very much to be desired.

There are, of course, surgical instruments which utilize a flexible blade sliding in two parallel grooves. For example, U.S. Pat. No. 2,131,780 to Story entitled, "Adenotome", issued Oct. 4, 1938, refers to an adenotome of the rigid type, as follows: The "moving part of the frame is secured to a blade which moves in a curved track formed by parallel-wall grooves, opening toward each other and the forward end of this blade is sharpened to provide the cutting element." While the quoted passage applies literally to an element of my new meniscatome, there is no teaching in that, or in other adenotome patents, of an instrument suitable for a meniscectomy, for at least two reasons. First, the two blade guides of the adenotome are in a permanently fixed relation. Those of my meniscatome come apart, to allow the grooved blade guides to be placed within a knee joint. No adenotome could ever be placed in the posterior knee joint for meniscectomy. The second reason is that the shape of the adenotome guides is contoured and shaped to fit into the posterior pharynx but could never be introduced into the posterior knee in relation to the periphery of the meniscus as is necessary for meniscectomy.

Other patents showing grooved guides for a flexible cutting blade include Grieshaber U.S. Pat. No. 2,258,287, issued Oct. 7, 1941, for an "adenotome"; Diamant U.S. Pat. No. 1,339,692, issued May 11, 1920, for an adenotome; and Storz 2,843,128 issued July 15, 1958, for an "Adenotome".

The primary object of this invention is to provide an instrument that will assist a surgeon in performing a meniscectomy.

Another object of this invention is to provide an instrument useful in performing a meniscectomy in which the operation can be performed with precision and exactness in an improved manner.

A further object of the invention is to provide an instrument for performing a meniscectomy in which there is a cleaner and smoother cut of the meniscus in an intra-articular fashion at the meniscal base than has previously been possible as regards the posterior meniscus.

Still another object of the invention is to provide an instrument for performing a meniscectomy with less bleeding from the posterior synovia than is often produced by conventional surgical instruments and by special meniscal instruments, such as the Lowe-Breck or Smillie knives.

An additional object of the invention is to provide a surgical instrument that will reduce the time and trauma required for performing a meniscectomy.

Moreover, it is the object of the invention to provide an instrument that will reduce the recovery time for a patient who has had a meniscectomy.

Still another object of the invention is to provide an instrument which will eliminate the need for a second incision into the joint posteriorly for detachment of the posterior meniscus.

SUMMARY OF THE INVENTION

My flexible blade meniscatome was thus developed for solving the above-mentioned problems. A key to the development was the recognition of the facts that (1) a normal intraarticular pocket or channel exists both below the meniscus and between the tibia and the coronary ligaments that attach to the base or periphery of the meniscus, and (2) a second pocket or channel of similar type is located above the meniscus, between the femur and the adjacent synovia. It was into these normal anatomic channel pockets that grooved guides of proper contour (similar in configuration to the configuration of the normal meniscus) are individually inserted. Once these guides are in the knee joint, they are locked together. This positions the grooves to carry a flexible cutting blade around the meniscal periphery in a precise, controlled fashion. The foregoing procedure not only protects the synovia but detaches the meniscus in its base in the line of meniscal fibers so as to leave a thin edge of meniscal base (about one sixteenth-inch) with attached synovia above and coronary ligaments below. It actually accomplishes an intra-articular meniscal detachment of the posterior portion of the meniscus with exception of the horn.

The present invention involves a special instrument for effecting a precise controlled intra-articular smooth cutting action in the posterior periphery of the base of the meniscus adjacent to and inside of the synovia with less trauma and far less bleeding than has heretofore been possible. Two grooved guide members are respectively mounted upon separate handles. These two guide members have a shape generally conforming to the periphery of the posterior portion of the meniscus to be detached by the instrument. The grooved guide member have internal grooves facing each other and which are adapted to receive and channel a flexible cutting blade. The two handles are removably attachable to each other and to an overlying frame member which not only supports them but contains the cutting blade as well as the mechanism for driving the cutting blade. The frame member is bent upward at the base of the grooved guides to form a two-part frame with a 100° to 115° angle between said parts. The part of the frame member above and beyond the aforesaid bend supports the flexible cutting blade and also supports the means for driving the flexible cutting blade through the channel grooves in the guides.

With the new instrument the surgeon first, using a generally conventional surgical procedure, detaches the anterior portion of the meniscus. He then inserts the two grooved guide members, one at a time, in an intra-articular manner as described above. He respectively positions them in the normal anatomic synovial pouches above and below the meniscus. The handles of the grooved guide members may then be locked or otherwise rigidly affixed to each other and then to the frame member. It is then possible by driving the cutting blade along grooved channels in the guide members to cause that blade to follow the periphery of the posterior base of the meniscus and thus detach the posterior portion thereof from its thin meniscal base, leaving the thin meniscal base, the femoral synovia and the coronary ligaments intact.

Figures 1, 3, 4, 8:
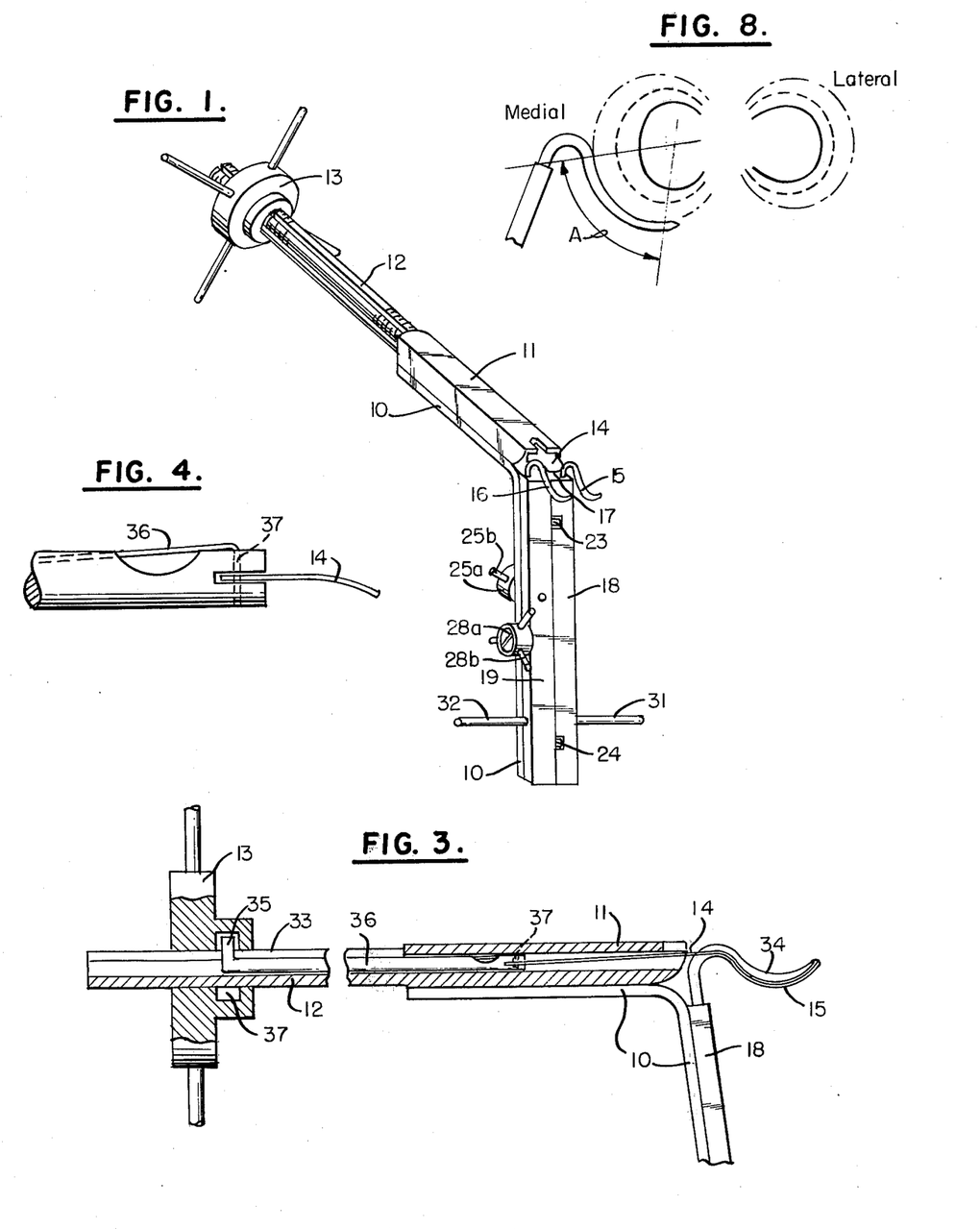
FIG. 1 is a perspective view of the new surgical instrument in assembled condition.
FIG. 3 is a cross-sectional view of the surgical instrument of FIG. 1, showing the details of the crank for driving the blade in either direction along the grooved channels in the guides.
FIG. 4 is a detailed view of the cutting blade and the means for attaching the cutting blade to its drive shaft.
FIG. 8 illustrates how the shape of the curved grooved guide means for the blade was obtained for both the medial and lateral menisci.

The two grooved guides both have a configuration conforming to the portion of the meniscus designated between solid lines by the letter "A" in FIG. 8.

As stated above, the overlying cutting blade frame has two portions in continuity positioned at an angle of about 100° to 115° to each other. If this angle is considerably greater, for example 135°, the cutting blade frame portion of the instrument will obscure the surgeon's vision after the instrument is in position in the knee joint so that the application of traction on the anterior meniscus by the surgeon is obstructed and impaired.

A summary of the surgical procedure, using my new instrument, for detaching a meniscus, is as follows:
1. Incision favored. Anterior transverse at joint level. Partellar ligament to collateral ligament.
2. Enter the joint through a transverse incision above the level of the meniscus, extending from the fat pad to the collateral ligament. Detach the anterior meniscus in its base one sixteenth-inch inside of the synovial attachment and roughly in the frontal plane.
3. Insert the flexible blade meniscatome.
    a. Choose the grooved guides having proper size.
    b. With the knees at 165°, place the angle of the curved grooved guide beneath the patellar ligament, thus orienting the tip of this guide intra-articularly beneath the meniscus, adjacent the tibia, the meniscus, and coronary ligaments and deep to the collateral ligament.
    c. As the tip of the grooved guide is inserted into this normal anatomic pocket or channel, the grooved guide handle is rotated posteriorly in the horizontal plane, causing the curved grooved guide to follow the inferior periphery of the meniscus intra-articularly.
    d. Next, the mated guide of same size is inserted above the meniscus into the synovial pocket or channel formed by the meniscus, the femur and the synovia, deep to the collateral ligament.
    e. The two grooved guides, one above and one below the meniscus, are advanced into the posterior knee joint without force and are then meshed and fixed to each other by the screw lock nut mechanism.
    f. The frame is next meshed with the two curved guides by orienting the guide pins to allow fixation of the frame to the grooved guides by a screw lock nut mechanism.
    g. Advance the flexible cutting blade tip to the entrance of the grooved channels in the grooved guides. With traction of the detached anterior meniscus, a scalpel point is used to nip the meniscus base, about one sixteenth inch inside of the synovial attachment, at the point where the flexible blade tips enter the grooves in the guides. This starts the blade into the meniscal fibers which are to be released.
    h. Advancement of the flexible cutting blade into the base of the meniscus partly detaches the posterior meniscus intra-articularly.
    i. The flexible cutting blade is retracted about five eight inch and the knee is gently flexed to 100°. Gently press the guide handle advancing the grooved guides around the posterior tibia so that the tip of the grooved guides face the posterior meniscal insertion. Again, advance the cutting blade into the grooved channels of the guides---gently---. STOP when resistance is encountered. CAUTION: Do not flex the knee past 100° when the instrument is within the joint. This avoids impingement.
    j. Remove the instrument by reversal of the procedure of insertion.
    k. Traction applied to the anterior meniscus then displaces the meniscus into the intercondylar notch.

A special curved posterior horn knife is inserted between the tibia and femur, touching the remaining attachment of the posterior horn of the meniscus. As traction is applied to the detached anterior horn, the forward cutting edge on the special posterior horn knife is pressed against the tightened meniscal elements which are holding the posterior horn. Thus, further release of the meniscus is accomplished. When only the horn attachment remains, it is cut loose using scissors through the intercondylar notch.

4. Closure is anatomical layers after hemostasis completes the operation.

DETAILED DESCRIPTION OF THE INVENTION

In FIG. 1 the new surgical instrument has a main cutting frame support 10 to which is permanently attached a tubular cutting blade holder 11. The tubular member 11 is rigidly attached to the cylindrical tube 12 which has external threads upon which the driving crank 13 rotates. When the crank 13 is rotated clockwise (looking from the rear), the blade 14 is moved forward according to the familiar screw-jack principle and enters slits or grooves in the inner (facing) side walls of rigid grooved guide members 15 and 16 which guide the highly flexible blade 14 along a predetermined path, as will be explained hereinafter. The forward edge of blade 14 is a sharp edge 17 so that it will perform the desired surgical cutting operation.

Figures 2, 9, 10:
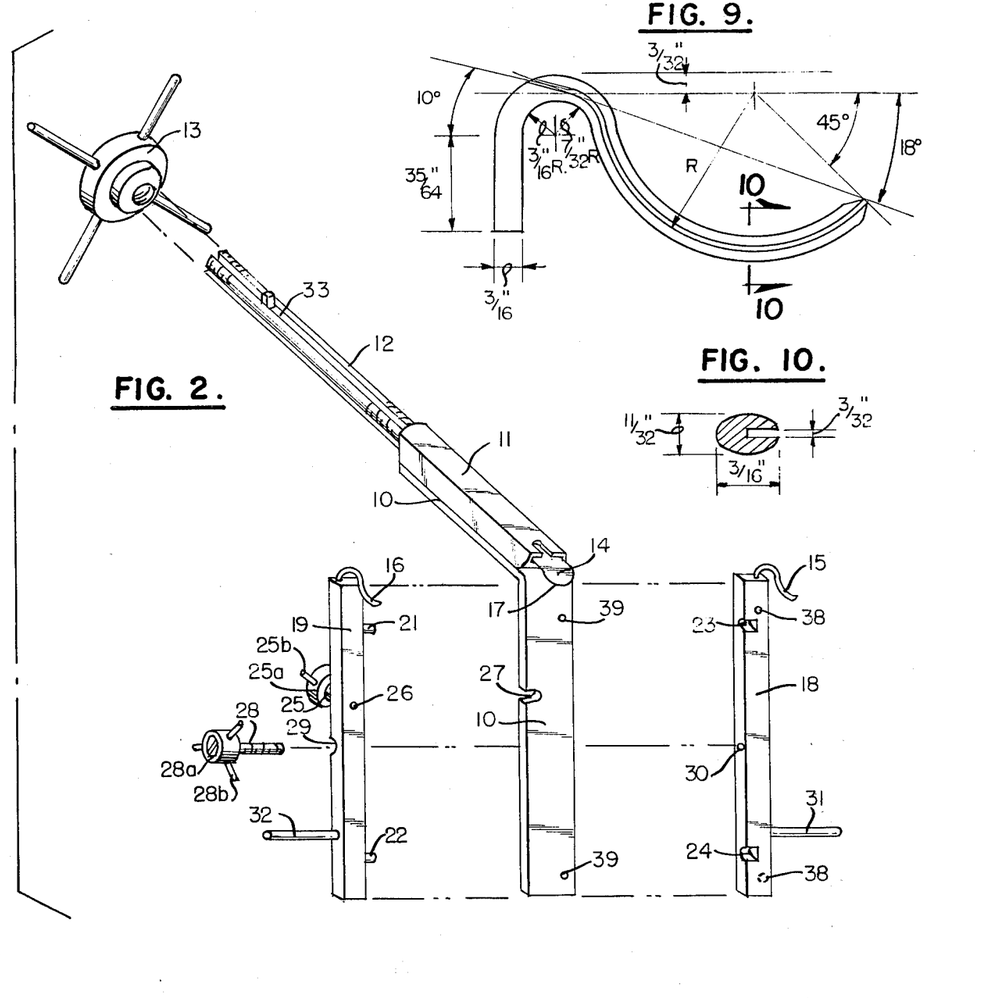
FIG. 2 is an exploded view of the surgical instrument of FIG. 1.
FIG. 9 is a more detailed view of one of the curved guides showing preferred dimensions, angles, etc.
FIG. 10 is a cross-sectional view taken along line 10-10 of FIG. 9.

As shown in FIG. 2, the guide members 15 and 16 are, respectively, a part of and carried by bars 18 and 19 which are adapted to be readily attached to member 10. Each of bars 18 and 19 is hereinafter referred to as a handle since it is held in the surgeon's hand for positioning the intra-articular grooved guide element or member (15 or 16) hereinafter described.

When the instrument is assembled after the two intra-articular grooved guide portions have been introduced into the posterior knee joint, handles 18 and 19 align by pins 21 and 22. The forward end of bolt 28 is permanently fixed in hole 13 of handle 18. This bolt passes through indent 29 in handle 19 and has nut 28a. The nut 28a may be tightened against the side of handle 19 to clamp handle 19 to handle 18. Handles 28b prevent rubber glove tearing by stresses manually applied when tightening nut 28a. Auxiliary handles 31 and 32 are respectively mounted on handles 18 and 19 in order to obtain rotary stress on the grooved guide members 15 and 16. Moreover, handles 31 and 32 assist in alignment and locking the instrument.

The next step in assembling the instrument is that frame 10 overlies the meshed and locked handles 18 and 19, as shown in FIG. 1. Pins 21 and 22 on handle 18 align the locked grooved guide handles 15 and 16 with frame 10. The forward end of bolt 25 is permanently fixed in hole 26 of handle 19. Bolt 25 extends outwardly through the indent 27 of frame 10 and has a nut 25a. When the nut 25a is tightened against frame 10 it clamps handle 19 to the frame 10. Since handle 18 is attached by bolt 28 and nut 28a to handle 19 before the latter is clamped to the frame 10, the clamping of handle 19 to the frame 10, as described above, in effect clamps both handles 18 and 19 to the frame 10. The threaded portion of bolt 25 passes through a slot in frame 10, that slot being unthreaded and being of slightly greater width than the diameter of bolt 25. Auxiliary handles 25b on the nut 25a are for prevention of rubber glove tearing by stress manually applied when tightening this bolt.

FIG. 3 shows the details of the means for driving the blade and is a cross-sectional side view with handle 19 omitted. The crank 13 has internal threads which mate with the threads of cylindrical tube 12 so that if the crank is rotated clockwise (looking from the left), the crank 13 moves toward the right. The externally threaded cylindrical tube 12 has a slot 33 in its upper wall, which slot connects the inner hole of the tube to the outside, thereby permitting the upstanding end 35 of the cutter blade push rod 36 to move along the tube 12 in said slot 33. The upstanding end 35 is captured within an internal annular space 37 of crank 13 so that as crank 13 moves forwardly and rearwardly, the rod 36 also moves forwardly or rearwardly, respectively. The forward end 37 of rod 36 is slotted to receive the flexible cutting blade (FIG. 4). A hole in the rear end of the flexible blade 14 is fixed to rod 36 by a pin (FIG. 4), so that the blade is driven forwardly or rearwardly in its channel as the crank 13 moves forwardly or rearwardly, respectively. It is unnecessary, in order to carry out the invention, to use the screw-jack force multiplying means, or any other force multiplying means, for driving blade 14 to the right (FIG. 3). For example, the threads on the outside of tube 12 and on the inside of crank 13 may be omitted so that the blade 14 may be advanced forwardly by pushing crank 13 forwardly and retracted rearwardly by pulling crank 13 rearwardly. When the blade 14 moves forwardly, its forward end moves outside of tubular member 11, and enters the two facing slits or grooves 34 in the guide members 15 and 16 respectively. Each of these slits begins at the inner part of its guide member 15 or 16, as the case may be, and extends laterally about half-way through the width of the grooved guide member 15 (or 16). Therefore, as appears in FIG. 3, when the crank 13 is rotated clockwise (as seen from the left), the blade 14 enters the left end of the slits 34 of the grooved guide members 15 and 16 and progresses forwardly in the grooved channel of the guide members 15 and 16 at the same rate that the crank 13 is moved forwardly.

Guide member 16, of course, has the same configuration as the guide member 15. The only difference between members 15 and 16 is that the slit 34 in guide member 15 is on that side of the guide member 15 which faces guide member 16 and the complementary slit 34 in guide member 16 is on the side of member 16 that faces member 15.

Figures 11, 12, 13:
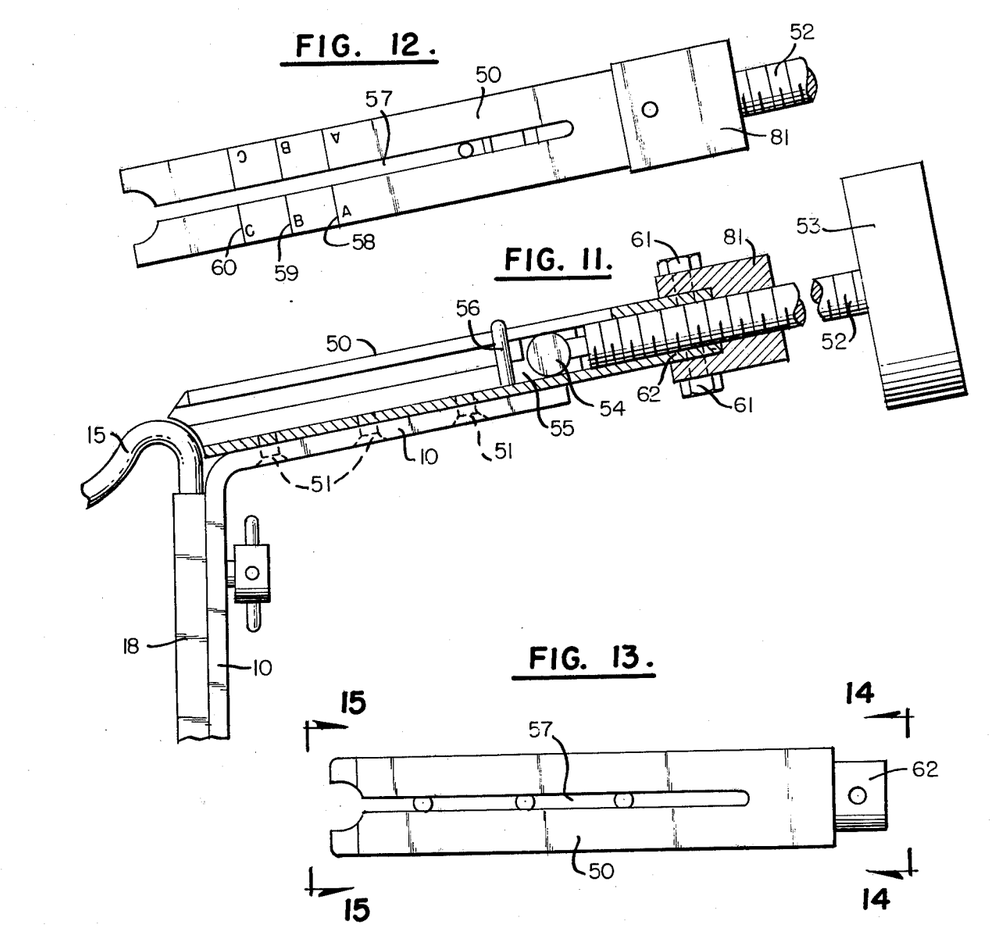
FIG. 11 is a side view of a modified form of the surgical instrument incorporating an improved blade driving means.
FIG. 12 is a top view of a portion of FIG. 11.
FIG. 13 is a top view of tube 50 of FIG. 11.
Figure 14:
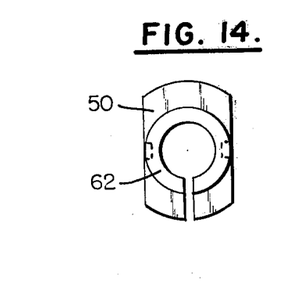
FIG. 14 is a front end view of the tube 50 of FIG. 11.
Figure 15:
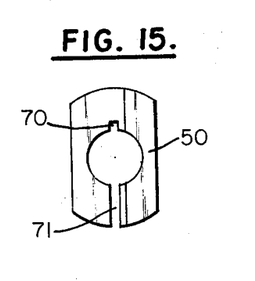
FIG. 15 is a rear end view of the tube 50 of FIG. 11.

In addition to the invention described in FIGS. 1 to 10, there is shown in FIGS. 11 to 13 of the drawings and described in this paragraph an improved form of blade driving means. The words "blade driving means" refer only to parts tube 50, tube 81, rod 52, knob 53, ball 54, and pin 56. This new blade driving means was devised after the apparatus of FIGS. 1 to 10 was invented and is not specifically claimed since it was developed by another in collaboration with me; however, the overall surgical instrument embodying the improved form of blade driving means is within the scope of the basic invention described in conjunction with FIGS. 1 to 10. FIG. 11 shows the main frame 10 supporting the handle 18 and guide 15 which are the same as in earlier figures. A tube 50 is held to the frame 10 by bolts 51 and receives rod 52 having outside threads which mate with the threads in the bore of tube 81. That tube is held by bolts 61 to tube 50. Handle or knob 53 enables the surgeon to move rod 52 forwardly and rearwardly according to the screw-jack principle. At the forward end of rod 52 is a ball 54 that is seated in a suitable socket located in guide member 55. That guide member, therefore, moves forwardly and rearwardly with the rod 52. A pin 56 extends from guide member 55 to which it is secured through the hole in the rear of the cutting blade 14 (not shown in FIG. 11) and also through the slot 57 running along the upper side of tube 50. The pin 56 will move along slot 57 and thus indicate to the surgeon the distance he has moved the blade. In this connection graduations 58, 59 and 60 (respectively representing positions A, B, and C) are helpful. As shown in FIGS. 13, 14 and 15 the tube 50 has a rearward portion 62 of reduced size for receiving tube 81. As shown by FIG. 15 (a drawing of the forward end of tube 50) the tube 50 has internal grooves 70 and 71 for receiving the side edges of the cutting blade 14. The blade-driving means of FIGS. 11 to 15, therefore, operates to move the blade 14 forwardly and rearwardly to advance the retract rod 52 which in turn advances and retracts guide member 55 with its pin 56, and pin 56 in turn advances and retracts the blade 14 (not shown in FIGS. 11 to 15).

Measurement of numerous normal knee X-rays chosen at random, using normal bony anatomic landmarks correlated to normal meniscal position for both the lateral and medial menisci, allowed determination of the largest medial and lateral menisci found, the average medial and lateral menisci found and the smallest medial and lateral menisci found. Graphically represented FIG. 8 shows the solid line to represent the smallest size medial and lateral menisci, the dashed line (———) the average size medial and lateral menisci, and the dash and dot line (—.—.—.) the largest size medial and lateral menisci encountered. These three sizes of guides, similarly contoured to the shape of the posterior meniscal periphery, are respectively represented by FIG. 5, FIG. 6, and FIG. 7. The letter, A, FIG. 8, indicates this posterior meniscal periphery at the base of the meniscus. Important and common to all grooved guide sizes is the angle shown to be 18° on FIG. 9. A variation ' or — of only about eight (8°) can be allowed because if this angle decreases excessively, the instrument cannot then be inserted into the posterior compartment of the knee. If this angle increases excessively, the flexible cutting blade cannot be made to negotiate the curve without requiring that it be too thin to function.

Each complete instrument (FIG. 1) is provided with these three different size grooved members 15S, 15M and 15L (these three being generically referred to as 15) along with three complimentary grooved guide members 16S, 16M, and 16L (these three being generically referred to as 16). Each of the guide members 15S, 15M, and 15L are mounted on a separate handle 18. The proper size of grooved guide member 15, to fit the patient is chosen and used when performing a given operation. It is also eviden, therefore, that there must be three separate handles 19 and three separate grooved guide members 16, so that there will be a mated grooved guide member to conform to the particular size grooved guide member 15.

The following table shows the dimention "R" for the three different sizes of guides, namely, Size "S", Size "M" and Size "L":

| SIZE | R |
| --- | --- |
| S | 17/32 |
| M | 11/16 |

-continued

| SIZE | R |
| --- | --- |
| L | 15/16 |

Figure 5:
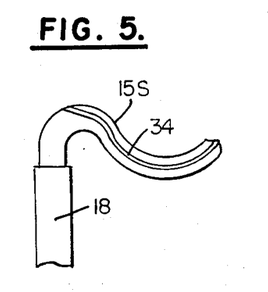
FIG. 5 is a side view of one of the intra-articular portions of the guide 15-S whose grooved channels carry the cutting blade; this guide being used for a small size meniscus of comparable size, whether it be medial or lateral.
Figure 6:
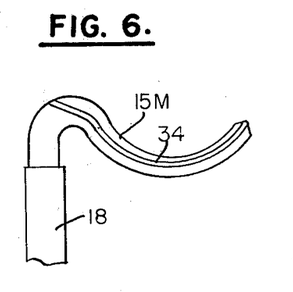
FIG. 6 is a side view of the intra-articular portion of the guide 15-M whose grooved channels carry the cutting blade; this guide being used for a medium size meniscus of comparable size whether medial or lateral.
Figure 7:
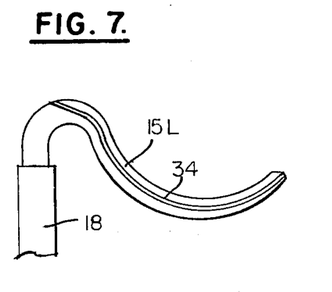
FIG. 7 is a side view of the intra-articular portion of the guide 15-L whose grooved channels carry the cutting blade; this guide being used for a large meniscus whether medial or lateral.

The original bristol board drawings filed with this application show the preferred sizes for guides 15S, 15M and 15L in FIGS. 5, 6 and 7. The reproduction of those figures as they will appear in the printed patent will, therefore, be about 70% of the preferred size.

The handle 18 is accurately positioned on the member 10 by means of pins 38 projecting rearwardly from the handle 18 and entering pinholes 39 and member 10.

It is noted that frame 10 (FIG. 3) has a horizontal portion 10 attached to tubular member 11, and a generally vertical portion 10 to which handles 18 and 19 are attached. The angle between these two portions of frame 10 should be properly selected for best results and generally is about 100° to 115°. If the angle is as large as 135° the tubular member 11 and 12 and crank 13 may interfere with the ability of the surgeon to see all of the details of the operation or to apply necessary traction on the detached anterior portion of the meniscus.

The method of using the surgical instrument described above to surgically detach the posterior part of a meniscus will next be described in some detail.

An anterior transverse incisional approach is favored.

Emphasis is laid upon the importance of avoiding gross knee contamination by the simple expedient of sterile preoperative preparation and wrapping the operative area on the day prior to surgery.

Repeat preparation in the operating room after extremity extraversation and pneumatic tourniquet application prepares the knee for draping. A bloodless field, thus created, is, of course, imperative to proper intra-articular inspection and meniscectomy.

The skin and subcutaneous incision thought best for this type meniscectomy is a short transverse incision at the level of the subchondral bone plate of the tibia when the knee is at 90 degrees. The incision extends from the patellar ligament to the collateral ligament. The extensor aponeurosis is divided in the line of the joint from the patellar ligament to the collateral ligament. Thus exposed is the underlying adipose layer, deep to the extensor aponeurosis, containing the genicular vessels which generally nearly overlie the meniscus. Instead of a transverse incision through these vessels the incision is slightly below them. Sharp dissection upward in the frontal plane, deep to the genicular, to above the level of the superior surface of the meniscus, allows synovial division from the fat pad to the collateral ligament. Systematic inspection of the interior of the joint grossly, as an assistant moves the knee when requested, is diagnostically helpful. When a decision is made to remove the meniscus, the front half is detached by sharp dissection so as to leave a thin meniscal base still attached to the coronary ligaments below and the synovia above. Thus, the anterior meniscal detachment is actually "intra-articular" and roughly in the frontal plane. By this technique the fat pad is not cut into nor disturbed. Continued sharp dissection of the meniscus anteriorly under direct visualization proceeds from the anterior horn to the collateral ligaments. Intra-articular insertion of the special chosen grooved guides of the "flexible blade meniscatome", (described in connection with FIGS. 1 to 7) into the posterior compartment of the knee is then carried out by channeling the grooved guides into the special normal anatomic pockets of the posterior compartment of the knee.

Prior to the beginning of the operation the crank 13 was rotated counterclockwise to retract blade 14 into the body of tubular member 11. Furthermore, the handles 18 and 19 together with their grooved guides 15 and 16 were detached from frame member 10, so that they may be individually inserted into the human knee separately with one above and one below the meniscus and lying in the normal synovial pocket.

With the knee at 165°, one of the guides 15 is inserted first by placing the angled portion thereof deep to the patellar ligament which orients the tip of the grooved guide in front of the collateral ligament, allowing the tip to enter the intra-articular space between the meniscus and the tibia. Motion of the grooved guide handle in the transverse plane posteriorly then advances and rotates the curved intra-articular portion into the posterior knee compartment pocket defined by the meniscus, the tibia, and the coronary ligaments. The second grooved guide 16 is then inserted into the synovial pocket between the meniscus and the femur. Next, the two grooved guides 15 and 16 are aligned and are then attached to each other by nut 28a and then to the frame 10 by nut 25a to thus assemble the instrument to the condition shown in FIG. 1. As thus assembled, the grooved guides 15 and 16 are within the posterior compartment of the knee joint.

With the knee at 165° and the grooved guides 15 and 16 in the posterior compartment of the knee, the surgeon next advances the cutting blade 14 by rotating crank 13 clockwise. The meniscus should be nipped at the guide groove entrance. As the flexible cutting blade 14 advances, approaching the entrance to the grooves, traction on the detached anterior meniscus, in an anterior direction, allows the point of the scalpel to nip the meniscus about one-sixteenth inch from the attached synovia and coronary ligaments at the groove entrance. This allows the cutting blade 14 to properly enter the guide slits or grooves 34. Thus, the blade 14 then enters the slits or grooves 34 of the intra-articular guides 15 and 16. Gentle traction on the meniscus is accompanied by advancing the cutting blade 14, using the screwjack mechanism 12, 13 and in this way detaching the meniscus at its base in an intra-articular fashion throughout most of its posterior extent in the line of the meniscal fibers. A thin "peripheral rind", about one-sixteenth inch thick, of the meniscal base remains attached to the synovia above and to the coronary ligaments below.

Displacement of the meniscus into the intercondylar notch by traction as well as the final posterior horn detachment is then undertaken in a generally conventional surgical fashion.

Removal of the instrument of FIG. 1 is in the reverse order of insertion.

I next consider the importance of hemostasis. Some surgeons express the same sentiment although a few actually accomplish this important feature. One reason why hemostasis is usually difficult prior to closure is due to the usual difficult conventional removal of the posterior half of the meniscus, which so badly tears up the synovia even though very careful dissection attempts, to avoid excess damage, are adhered to. Considerable bleeding from the divided and damaged synovia occurs when the tourniquet is released. Inadequate visualization of the posterior synovia, by virtue of the compact anatomy of the knee, makes for excessive difficulty in obtaining hemostasis, even when suction electrocoagulation is used simultaneously. All too often after some suction, some coagulation, some irrigation and even a second attempt at repeat suction-electrocoagulation and irrigation, closure of the synovia with persistent bleeding occurring into the joint is the usual actuality. Most hemorrhage comes from the posterior compartment.

Intra-articular amputation using the "flexible blade meniscatome" (the instrument of FIG. 1) which amputates the meniscus with negligible synovial damage, keeps bleeding in the posterior compartment to a minimum. Anterior hemostasis is, of course, easily accomplished by suction electrocoagulation under direct visualization. A combination of suction-electrocoagulation, using an insulated neurosurgical type suction tip, accomplishes hemostasis most efficiently with the least soft tissue damage. Latent synovitis, swelling, delayed tissue equilibrium, and prolonged convalescence seem directly related to the degree of hemostasis accomplishable prior to closure. After, and only after, complete hemostasis exists is wound closure begun. The surgeon should not close the wound and then release the tourniquet hoping to control bleeding by a pressure dressing.

Careful layer by layer closure begins with the synovia. The synovial edges are slightly everted reattaching the flap of the "coronary ligament-meniscal base-inferior synovia" to the superior synovia. An excess of small sutures carefully approximating the wound is generally used rather than inaccurate tissue apposition, using large sutures. Next, the adipose flap containing the previously avoided genicular vessels, is then pulled back down over the synovial repair, reattaching it at its original site. The extensor aponeurosis is likewise carefully closed, as is the vaginal fascia, subcutaneous layer, and skin. Dead spaces and exposed raw edges are kept to a minimum.

Sterile dressings and a light cylinder cast complete the procedure. Control of excess pain by use of a cast for the firsst 48 hours seems to make the patient less afraid of early motion. An ounce of early active motion seems to be worth a pound of "effleurage", "petrissage" and other modalities later.

COMPARISON OF PRIOR ART MENISCECTOMY WITH THE ONE DESCRIBED HEREIN

Menisci of the knee tear in a variety of ways. The tear may be peripheral and of varying extent (called "bucket handle" tears), small pedunculated flaps, L-shaped tears, or localized tears or fraying in the concave edge. Combinations of these basic types of meniscal tears also occur.

Generally speaking most orthopedic surgeons favor total meniscectomy for traumatic separation of the posterior and middle portion of the cartilage. All peripheral separations or avulsions should be excised in toto.

a. The Surgical Incision

Many surgical incisions have been used to approach the menisci and are as follows:
1. Parapatellar (along side the patella or knee cap).
2. Medial curved approach (Fisher) (Cave) advocated by those who favor a posterior and anterior incisional approach.
3. Medial oblique or lateral oblique incision.
4. Many others too numerous to outline.

The anterior transverse skin incision extending from the patella ligament to the collateral ligament is favored, when my invention is practiced.

b. Instruments Used

Once the meniscus has been inspected directly, and when the knee is passively moved while the meniscus is probed, using a spatula—the true pathology is hopefully recognizable. Nonetheless, when the decision is made to do a meniscectomy the following instruments are available and have been customarily used in the past:

1. Scalpel — Detachable or fixed blade types.
2. Scissors — Mayo and Metzenbaum types.
3. Lowe-Breck cartilage knife (Fixed blade knife).
4. Smillie cartilage knives (Fixed blade knife).
5. Martin cartilage clamps.

When practicing my invention, I use these same instruments except that I replace the Smillie and Lowe-Breck knives with the instrument shown in the drawings of this application.

c. Anterior Detachment

Generally after the meniscus is approached through ones favorite incision and when the decision to remove the meniscus is made, the anterior half of the meniscus is detached from the supporting structures. In the past there has been a great variation in the technique of removing the anterior portion of the meniscus. In particular there has been intentional cutting of the coronary ligaments below the meniscus, the synovia above the meniscus, the entire meniscal base, and the fat pad adjacent to the meniscus. Others dissect the anterior portion of the meniscus in the frontal plane, detaching it intra-articularly near its base, thus leaving the coronary ligaments, the synovia, the meniscal base, and the fat pad undisturbed.

When practicing my invention, I use the anterior detachment, leaving the coronary ligaments below and the synovia above attached to the thin base of the meniscus. Such is accomplished by intra-articular meniscal detachment at the periphery of the meniscus. The fat pads, the synovia, the meniscal base, and the coronary ligaments are left undisturbed and intact.

d. Posterior Detachment

With the prior art form of operation, one proceeds as follows. Care is taken to avoid damage to the medial collateral ligament as the base of the meniscus is detached peripherally to the anterior edge of the collateral ligament. At this point, further detachment-release of the posterior portion of the meniscus is attempted by insertion of the Lowe-Breck knife or one of the Smillie knives. Traction is applied on the detached anterior meniscal element as the curved Lowe-Breck or Smillie fixed blade knife is forced nearly blindly posteriorly in an attempt to detach the posterior meniscus. Great difficulty is encountered; the synovia is "chewed up", the meniscus fragmented and a point is reached in the operation where most surgeons complain of great technical difficulty, of the inadequacy of the surgical knives which are being asked to perform a specific job, and of the tissue damage occurring. Excessive hemorrhage in the posterior compartment accompanies the excess soft tissue damage created.

A prior art variation in the technique of removal of the posterior portion of the meniscus is to make a second incision behind the collateral ligament entering the posterior compartment, both above and below the meniscus, allowing the anterior end of the meniscus to be pulled through into the second incision. At this point, the Lowe-Breck or Smillie knife is forced along the periphery of the meniscus posteriorly, most often detaching the meniscus by dividing the synovia. Alternatively, according to the prior art, the meniscus may be peripherally detached using sharp dissection with a scalpel. This is very difficult because of the depth of the dissection required through a very small incision.

The meniscus once detached peripherally is pulled through the joint into the intercondylar notch. Effort is made to visualize the posterior attachment at the posterior horn in order to divide its attachment and thus completely free the meniscus.

In contrast, and in accordance with my invention, the posterior detachment of a meniscus is accomplished as follows. The flexible blade meniscatome shown in the drawings of this application is inserted into the posterior compartment of the knee, as hereinbefore described in detail. The cutting blade is advanced, detaching the meniscus in its base at the periphery and to a point approaching the posterior horn.

I claim to have invented:

1. A surgical instrument comprising:
    a flexible cutting blade having a cutting edge,
    means for advancing the cutting blade with said cutting edge constituting the leading edge of the moving blade to perform a surgical cutting action, and
    guide means, having separate spaced projecting portions respectively insertable in at least two spaced openings of the knee that extend along the periphery of the posterior meniscus, for guiding said flexible cutting blade along a path substantially at the periphery of the posterior portion of the meniscus.

2. A surgical instrument as defined in claim 1 in which the last-named means comprises curved grooved guide means for guiding said flexible cutting blade in a path within the posterior meniscus at the periphery of the base portion of the meniscus that is adjacent to the synovia and coronary ligaments.

3. A surgical instrument as defined in claim 2 in which said curved grooved guide means comprises:
    two separate grooved guides separately insertable after surgical detachment of the anterior portion of the meniscus one of which guides is insertable intra-articularly above the posterior portion of the meniscus to be detached and the other of which guides is insertable intra-articularly below the posterior portion of the meniscus to be detached, and
    means for securing said two guides together in fixed relation to each other after they have been inserted into the posterior compartment of the knee joint.

4. The method of utilizing first and second curved guides each having the same curvature and which curvature conforms substantially to the curvature of the periphery of a posterior portion of a meniscus for detachment of a posterior portion of a meniscus from its support comprising:
    inserting the first of the two curved guides into the posterior knee compartment between the tibia, meniscus, and coronary ligaments to a position extending adjacent to the periphery of the posterior portion of the meniscal base to be detached,
    inserting the second of the two curved grooved guides into the synovial pocket between the meniscus, femur, and synovia to a position extending adjacent the periphery of the posterior portion of the meniscal base to be detached,
    holding said guides in a fixed relationship to each other, passing a cutting tool into the posterior portion of the meniscal base to be detached, and guiding said cutting tool by the aforesaid curved guides to detach said posterior portion.

5. A surgical instrument for detaching a greater part of the posterior portion of the meniscus from its support comprising:

a flexible elongated cutting blade having a cutting edge at one end and having two longitudingal side edges, first blade guiding means for insertion below the meniscus and between the tibia and coronary ligaments that attach to the base of the meniscus comprising a curved grooved guide and an elongated handle therefor, said handle and said blade guide being in substantialy the same plane, second blade guiding means for insertion intra-articularly into the synovial pocket above the meniscus, and between the femur and the adjacent synovia comprising a curved grooved blade guide and an elongated handle therefor, said handle and said grooved blade guide being in substantially the same plane, said first and second blade guiding means being separate from each other to permit them to be separately inserted into the knee, said curved grooved blade guides each having substantially the same size and curvature, and when held in complementary positions, said guides defining complementary grooves, that receive said two side edges respectively, for guiding a flexible cutting blade along a predefined path adjacent the periphery of the posterior portion of the meniscal base, a frame having an elongated portion for supporting both of said handles, means for securing said handles to said elongated portion of said frame for insuring that said curved grooved guides assume the aforesaid complementary positions so that their respective grooves will guide a flexible cutting blade, said frame having a change in direction adjacent the base of said grooved guides when they are mounted on the frame, to provide an extended portion of the frame which extends in a direction away from and generally aligned with those ends of said grooves which are closest to the handles, and driving means mounted on said extended portion of the frame for driving said blade with said cutting edge at the forward end of the moving blade and said side edges moving along said grooves respectively so that said blade will follow the curvature of said grooved guides and detach a meniscus accordingly.

6. A surgical instrument as defined in claim 5 in which said change of direction is sufficiently small that the extended portion of the frame and said driving means does not substantially interfere with the ability of the surgeon to observe the operation as it proceeds and so that room is allowed for traction on the initially detached anterior meniscus.

7. A surgical instrument as defined in claim 6 in which the grooved blade guides have the curvature of that peripheral portion of a meniscus which is designated A in FIG. 8 of the drawing.

8. A surgical instrument as defined in claim 6 in which the grooved blade guides have the shape of that posterior portion of the periphery of a meniscus in which the surgical cutting action is desired.

9. A surgical instrument as defined in claim 5 in which said change of direction is an angle on the order of 100°–115°.

10. A surgical instrument as defined in claim 9 in which the grooved blade guides have the curvature of that portion of a meniscus which is designated A in FIG. 8 of the drawing.

11. A surgical instrument as defined in claim 9 in which the grooved blade guides have the shape of that posterior portion of the periphery of a meniscus along which a surgical cutting action is desired.

12. A surgical instrument as defined in claim 5 in which the grooved blade guides have the curvature of that peripheral portion of a meniscus which is designated A in FIG. 8 of the drawing.

13. A surgical instrument as defined in claim 5 in which the blade guides have the shape of that posterior portion of the periphery of a meniscus in which a surgical cutting action is desired.

14. A surgical instrument as defined in claim 5, in which the angle between each said guide and its complementary handle is such that the guide may be inserted in a space adjacent the meniscus to position the guide along the periphery of a portion of the meniscus.

15. A surgical instrument for detaching a portion of the meniscus from its support comprising:

first and second curved blade guides each having substantially the same curvature as the other, first and second separate elongated handles for said first and second curved blade guides, respectively, each of said guides extending from one end of its elongated handle, being in substantially the same plane as said elongated handle, and including means for guiding a flexible blade along a curved path, a frame, a thin flexible cutting blade, means for attaching said handles to each other, means for attaching said handles to said frame to position the guides to receive said blade and guide it along said curved path, and means carried by said frame for driving said flexible blade in said curved blade guides so that said blade follows a path conforming to the curvature of said blade guides.

16. A surgical instrument for detaching a portion of the meniscus from its support as defined in claim 15 in which said curvature substantially conforms to the outer periphery of the posterior portion of a meniscus.

17. A surgical instrument for detaching a portion of the meniscus from its support as defined in claim 15 in which said curvature substantially conforms to the outer periphery of that posterior portion of a meniscus that is adjacent to the synovia and coronary ligaments.

18. A surgical instrument for detaching a portion of the meniscus from its support as defined in claim 15 in which said curvature substantially conforms to the outer periphery of that portion of a meniscus which is designated by the letter "A" in FIG. 8 of the drawings.

19. A surgical instrument comprising:

cutting means;

guide means for guiding said cutting means along a path substantially near the periphery of the posterior portion of a meniscus, said guide means comprising a guide element having a curvature conforming to the curvature of the periphery of the posterior portion of a meniscus and insertable in a space in a knee that is adjacent said posterior portion of a meniscus with the curvature of said element conforming to the curvature of the periphery of said posterior portion of the meniscus, and driving means for advancing said cutting means along said guide means to detach the posterior meniscus.

20. A surgical instrument as defined in claim 19 in which said guide means comprises two separate guides, each of said guides having a guiding portion of a shape substantially conforming to the periphery of the posterior portion of a meniscus, one of said guides being adapted to be inserted intra-articularly above the meniscus to a position where it extends along a path substantially conforming to the periphery of the posterior portion of a meniscus, the other of said guides being adapted to be inserted intra-articularly below the meniscus to a position where it extends along a path substantially conforming to the periphery of the posterior portion of a meniscus.

21. A surgical instrument comprising:

cutting means, guide means for guiding said cutting means along a path substantially near the periphery of the posterior portion of a meniscus, in which said guide means comprises two separate guides, each of said guides having a guiding portion of a shape substantially conforming to the periphery of the posterior portion of a meniscus, one of said guides being adapted to be inserted intra-articularly above the meniscus to a position where it extends along a path substantially conforming to the periphery of the posterior portion of a meniscus, the other of said guides being adapted to be inserted intra-articularly below the meniscus to a position where it extends along a path substantially conforming to the periphery of the posterior portion of a meniscus, each said guide having a handle separate from the handle of the other guide, and driving means for advancing said cutting means along said guide means to detach the posterior meniscus.

22. A surgical instrument as defined in claim 21 including a frame, means for rigidly attaching said handles to said frame after the guides have been inserted into the knee of a patient with one such guide above and one below the meniscus to be detached thereby securing said handles and guides in a fixed relation to each other, said frame carrying said driving means.

23. A surgical instrument as defined in claim 22 in which said frame is a bar having two portions that have an angle of about 100° between them, said driving means being carried by one of said portions, and said handles being carried by and being detachably secured to the other of said portions.

24. A surgical instrument as defined in claim 23 in which said cutting means comprises a flexible blade having a cutting edge at one end, and said guides having complementary grooves for guiding the flexible blade when said handles are secured to said frame.

25. A surgical instrument as defined in claim 22 in which said frame is a bar having two portions, said two portions being integral and having an angle between them that permits use of the instrument to perform a meniscectomy without either of the portions obscuring the surgeon's view of the operation, said driving means being carried by one of said portions, and said handles being carried by and being detachably secured to other of said portions.

26. The method of detaching the posterior portion of a meniscus after surgical entry into the knee and preliminary detachment of the anterior portion of the meniscus using a surgical instrument that has cutting means, two separate guides which coact to guide said cutting means, each of which guides has a separate handle, each said guide substantially conforming in shape to the periphery of the posterior portion of a meniscus, driving means for advancing the cutting means along the guides, a frame having first and second portions that are at an angle to each other, said driving means being carried by the first said portion, said handles being detachably secured to the second of said portions, and said handles being detached from said frame when use of the surgical instrument in the operation begins, comprising:

separately inserting said guides intra-articularly into a knee to position one of said guides beneath the meniscus so that it extends along the lower periphery of the posterior portion of the meniscus, and to position the other guide above the meniscus so that it extends along the upper periphery of the posterior portion of the meniscus, thereafter securing said handles to said second portion, and subsequently operating said driving means to advance said cutting means along said guides and in a path substantially conforming to the periphery of the posterior portion of the meniscus to thereby detach the meniscus.

27. The method of detaching the posterior portion of a meniscus after surgical entry into the knee and preliminary detachment of the anterior portion of the meniscus, using a surgical instrument that has cutting means, two separate guides which coact to guide said cutting means, each of which guides has a separate handle, each said guide substantially conforming in shape to the periphery of the posterior of a meniscus, driving means for advancing the cutting means along the guides, a frame having first and second portions that are at an angle to each other, said driving means being carried by the first said portion, and handles being detachably secured to the second of said portions, and said handles being detached from said frame when use of the surgical instrument in the operation begins, comprising:

position the thigh and the leg at an angle to each other that will facilitate insertion of the guides into the knee in the manner hereinafter described, separately inserting said guides to position one of said guides beneath the patellar ligament thus orientating the tip of this guide intra-articularly, in front of the collateral ligament beneath the meniscus into the space bounded by the tibia, the meniscus and the coronary ligament, and to position the other of said guides intra-articularly above the meniscus into the synovial pocket formed by the meniscus, the femur and the synovia, thereafter advancing the guides into the posterior joint and until the curvatures of the guides conform to the periphery of the posterior portion of the meniscus, subsequently securing the handles of said guides to each other and then to the second portion of said bar, and thereafter operating the driving means to advance the cutting means along said guides to detach the posterior meniscus.

28. The method as defined in claim 27 in which the following steps are carried out after the menicus is detached:

retract the cutting blade about five-eighths inch, flex the knee until the angle between the thigh and leg is about 100°, advance the guides further into the joint so that their forward tips generally face the posterior meniscal insertion, again gently advance the cutting blade until resistance is encountered, retract the cutting blade completely from the guides, detach the guide handles from said second portion, and remove the two guides from the knee.

29. The method of detaching the posterior portion of a meniscus after the knee has been surgically entered and the anterior portion of the meniscus has been detached, using a surgical instrument that has cutting means, two separate guides which coact to guide said cutting means, each of which guides has a separate handle, each said guide substantially conforming in shape to the periphery of the posterior portion of a meniscus, driving means for advancing the cutting means along the guides, a frame having first and second portions that are at an angle to each other, said driving means being carried by the first of said frame portions, said handles being detachably secured to the second of said frame portions, and said handles being detached from said frame when use of the surgical instrument in the operation begins, comprising:

insert the two guides, intra-articularly, separately with one above and one below the posterior portion of the meniscus, position the guides separately so that they follow the periphery of the posterior portion of the meniscus, thereafter secure the guide handles to each other and to said second portion of said frame, thereafter operate the driving means to advance the cutting means along said guides to thus detach the posterior meniscus.

withdraw the cutting blade means out of the guides, detach the guide handles from said second portion of said frame, detach the guide handles from each other, and thereafter separately remove the guides from the knee.

30. The method as defined in claim 29 in which the following step is performed after the meniscus is detached and before the handles are detached from the frame:

retract the cutting means, place the limbs that join at the knee at an angle of about 100°, reposition the guides so that their tips face the posterior meniscal insertion, and gently advance the cutting means until resistance is encountered.

31. A surgical instrument comprising an elongated frame that has a first portion that extends for a substantial distance and a second portion at an angle to the first portion, one end of said first portion being connected to one end of said second portion, the other end of said first portion being a free end, an elongated cutting blade having a cutting edge at one end, means supporting said blade on said first portion and mounting said blade for movement along a path parallel to said first portion with the cutting edge of the blade on the end thereof farthest from the free end of said first position, first and second curved separate guides each having an elongated handle, said guides defining complementary grooves for receiving the side edges of said blade and guiding the blade as it is moved into the guides, and mounting means for detachably mounting said elongated handles to said second portion and in parallel relation thereto to position open ends of said grooves in a position to receive the cutting blade as the cutting edge moves in a direction away from the free end of said first portion.

32. A surgical instrument as defined in claim 31 in which said curved guides have a curvature conforming to the posterior portion of a meniscus to be detached.

33. A surgical instrument as defined in claim 31 in which one of said handles includes threaded means operable to clamp said handles together.

34. A surgical instrument as defined in claim 31 in which said mounting means includes means for clamping one of said handles to said second portion.

35. A surgical instrument as defined in claim 31 in which said curved guides have a configuration conforming to the posterior portion of a meniscus to be detached, one of said handles including threaded means operable to clamp said handles together, said mounting means comprising means for clamping one of said handles to said second portion, and said angle being about 100°.

36. A surgical instrument as defined in claim 31 in which said angle is in the order of 100 to 115°.

37. A surgical instrument comprising:

a flexible cutting blade having a cutting edge, means for advancing the cutting blade to perform a surgical cutting action, and guide means for guiding said flexible cutting blade along a path substantially at the periphery of the posterior portion of a meniscus, in which said guide means comprise:

first and second guides each having a handle, each said guide and its handle having the shape relative to each other that is shown in conjunction with the guide and handle of FIG. 7.

* * * * *